United States Patent
Kuroda et al.

(10) Patent No.: US 8,574,372 B2
(45) Date of Patent: Nov. 5, 2013

(54) NOZZLE CLEANING METHOD, NOZZLE CLEANING DEVICE, AND AUTOMATIC ANALYZER

(75) Inventors: Akihisa Kuroda, Shizuoka (JP); Mitsuhisa Kobayashi, Shizuoka (JP); Yoshihiro Kase, Shizuoka (JP); Tamotsu Okawa, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 1022 days.

(21) Appl. No.: 12/615,005

(22) Filed: Nov. 9, 2009

(65) Prior Publication Data

US 2010/0051060 A1 Mar. 4, 2010

Related U.S. Application Data

(63) Continuation of application No. PCT/JP2008/057848, filed on Apr. 23, 2008.

(30) Foreign Application Priority Data

May 11, 2007 (JP) ................................. 2007-126905

(51) Int. Cl.
*B08B 9/093* (2006.01)

(52) U.S. Cl.
USPC ...... 134/22.18; 134/21; 134/22.1; 134/22.11; 134/22.12

(58) Field of Classification Search
None
See application file for complete search history.

(56) References Cited

FOREIGN PATENT DOCUMENTS

| JP | 62-228954 A | 10/1987 |
|----|-------------|---------|
| JP | 62-242858 A | 10/1987 |
| JP | 01-141537 A | 6/1989 |
| JP | 04-169851 A | 6/1992 |
| JP | 05-164764 A | 6/1993 |
| JP | 2002-040035 A | 2/2002 |
| JP | 2004-251797 A | 9/2004 |
| JP | 2005-241442 A | 9/2005 |
| JP | 2007-093220 A | 4/2007 |

OTHER PUBLICATIONS

English Translation International Search Report from PCT/JP2008/057848, dated Jul. 29, 2008 (4 pages).

*Primary Examiner* — Eric Golightly
(74) *Attorney, Agent, or Firm* — Kilpatrick Townsend & Stockton LLP

(57) ABSTRACT

A nozzle cleaning method includes cleaning an outer wall of a dispenser nozzle after liquid is sucked and before the liquid is discharged and cleaning at least an inner wall of the dispenser nozzle after the liquid is discharged.

4 Claims, 7 Drawing Sheets

NOZZLE CLEANING METHOD, NOZZLE CLEANING DEVICE, AND AUTOMATIC ANALYZER

CROSS-REFERENCE TO RELATED APPLICATIONS

This application is a continuation of PCT international application Ser. No. PCT/JP2008/057848 filed on Apr. 23, 2008 which designates the United States, incorporated herein by reference, and which claims the benefit of priority from Japanese Patent Application No. 2007-126905, filed on May 11, 2007, incorporated herein by reference.

BACKGROUND OF THE INVENTION

1. Field of the Invention

The present invention relates to a nozzle cleaning method for cleaning a dispenser nozzle through which liquid is sucked and discharged, a nozzle cleaning device, and an automatic analyzer.

2. Description of the Related Art

Conventionally, automatic analyzers have a nozzle cleaning device that cleans a dispenser nozzle, to avoid carry over that affects a result of analysis with a previously-dispensed specimen adhering onto the dispenser nozzle and being brought into a next specimen dispensation. This nozzle cleaning device is provided at an intermediate position along a path on which the dispenser nozzle moves between a position at which the specimen is sucked and a position at which the specimen is discharged, and is configured to provide cleaning fluid to the dispenser nozzle. In a nozzle cleaning method using this nozzle cleaning device, the dispenser nozzle is moved to the position of the nozzle cleaning device after a dispensation is completed by sucking and discharging the specimen, and the dispenser nozzle is cleaned by cleaning fluid provided to this dispenser nozzle (for example, refer to Japanese Laid-open Patent Publication No. 2005-241442).

SUMMARY OF THE INVENTION

A nozzle cleaning method according to an aspect of the present invention includes cleaning an outer wall of a dispenser nozzle after liquid is sucked and before the liquid is discharged; and cleaning at least an inner wall of the dispenser nozzle after the liquid is discharged.

A nozzle cleaning device according to another aspect of the present invention includes a cleaning vessel that has an opening, to which a dispenser nozzle is inserted, at an upper part thereof; a jet cleaning-fluid supplying unit that jets out cleaning fluid at an upper part in the cleaning vessel; a retention unit that is arranged in the cleaning vessel at a position below the cleaning fluid jet by the jet cleaning-fluid supplying unit and retains the cleaning fluid, the retention unit having an opening, to which the dispenser nozzle is inserted, at an upper part thereof; and a retention cleaning-fluid supplying unit that supplies the cleaning fluid to the retention unit.

An automatic analyzer according to still another aspect of the present invention has a dispenser nozzle with which liquid is sucked and discharged, dispenses the liquid into a predetermined vessel with the dispenser nozzle, and analyzes reaction liquid obtained by mixing different liquids in the vessel to react with each other, and includes a mode switching unit that has a special cleaning mode, in which an outer wall of the dispenser nozzle is cleaned after the liquid is sucked and before the liquid is discharged and at least an inner wall of the dispenser nozzle is cleaned after the sucked liquid is discharged, and a regular cleaning mode, in which the outer wall and the inner wall are cleaned only after the sucked liquid is discharged, the mode switching unit configured to switch between the special cleaning mode and the regular cleaning mode in accordance with analysis information obtained in advice.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
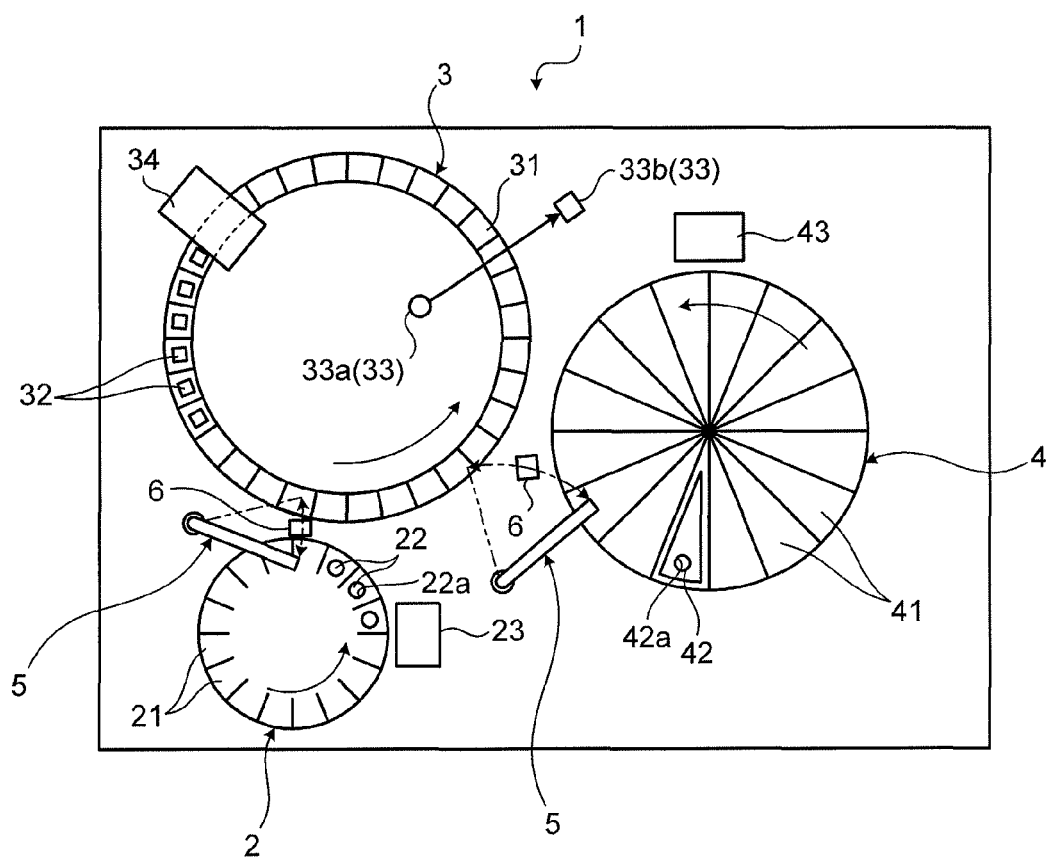
FIG. 1 is a schematic configuration diagram showing an automatic analyzer according to an embodiment of the present invention.

Exemplary embodiments of a nozzle cleaning method, a nozzle cleaning device, and an automatic analyzer according to the present invention are described in detail below with reference to the accompanying drawings. FIG. 1 is a schematic configuration diagram showing an automatic analyzer according to an embodiment.

An automatic analyzer 1 analyzes constituent concentration and the like of a specimen by measuring optical characteristics of reaction liquid that is obtained by mixing the specimen (liquid), such as blood and urine, and a reagent corresponding to a test item. The automatic analyzer 1 includes a specimen mounting unit 2, a reaction unit 3, a reagent mounting unit 4, a dispensing system (dispenser) 5, and a nozzle cleaning device 6.

The specimen mounting unit 2 has a disc-shaped table and a plurality of housing units 21 that are arranged at regular intervals along the circumferential direction of the table. In each of the housing units 21, a specimen vessel 22 that contains a specimen is housed. The specimen vessel 22 has an opening 22a that opens upward. The specimen mounting unit 2 is rotated in a direction shown by an arrow in FIG. 1 by a specimen-table driving unit (not shown). When the specimen mounting unit 2 is rotated, the specimen vessel 22 is moved to a specimen sucking position at which a specimen is sucked by the dispensing system 5.

An information recording medium (not shown) such as a barcode label, in which specimen information concerning a type of a contained specimen and an analytical item is recorded, is affixed to the specimen vessel 22. The specimen mounting unit 2 has a reading unit 23 that reads the information recorded in the information recording medium of the specimen vessel 22.

The reaction unit 3 has a disc-shaped table and a plurality of housing units 31 that are arranged at regular intervals along the circumferential direction of the table. In each of the housing units 31, a transparent reaction vessel 32 that contains reaction liquid obtained by making a specimen react with a reagent is housed in a state where an opening opens upward. The reaction vessel 32 is rotated in a direction shown by an arrow in FIG. 1 by a reaction-table driving unit (not shown). When the reaction unit 3 is rotated, the reaction vessel 32 is moved to a specimen discharging position at which a specimen is discharged by the dispensing system 5, or to a reagent discharging position at which a reagent is discharged by the dispensing system 5.

Furthermore, the reaction unit 3 has a measurement optical system 33. The measurement optical system 33 includes a light source 33a and a photometer sensor 33b. The light source 33a emits analysis light of a predetermined wavelength (340 nm to 800 nm). The photometer sensor 33b measures a light flux that has been emitted from the light source 33a and has passed through the reaction liquid in the reaction vessel 32. The reaction unit 3 has a cleaning system 34 that discharges the reaction liquid, for which the measurement has been finished, from the reaction vessel 32 and cleans the reaction vessel 32.

The reagent mounting unit 4 has a disc-shaped table and a plurality of housing units 41 that are arranged at regular intervals along the circumferential direction of the table. In each of the housing units 41, a reagent vessel 42 that contains a reagent is housed. The reagent vessel 42 has an opening 42a that opens upward. The reagent mounting unit 4 is rotated in a direction shown by an arrow in FIG. 1 by a reagent-table driving unit (not shown). When the reagent mounting unit 4 is rotated, the reagent vessel 42 is moved to a reagent sucking position at which a reagent is sucked by the dispensing system 5.

An information recording medium (not shown) such as a barcode label, in which reagent information concerning a type of a contained reagent and a contained amount is recorded, is affixed to the reagent vessel 42. The reagent mounting unit 4 has a reading unit 43 that reads the information recorded in the information recording medium of the reagent vessel 42.

Figure 2:
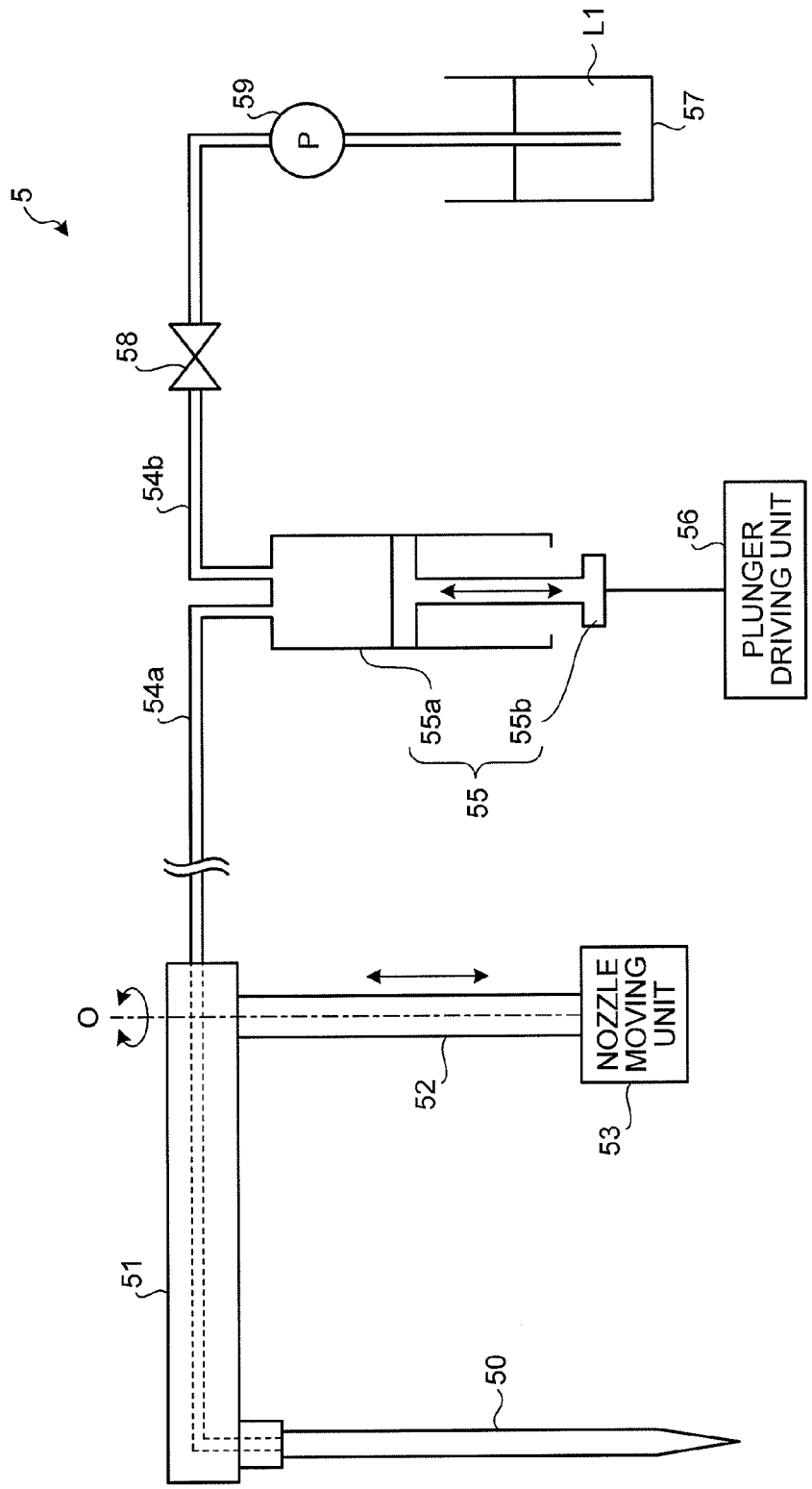
FIG. 2 is a schematic configuration diagram showing a dispenser.

The dispensing systems 5 are respectively provided between the specimen mounting unit 2 and the reaction unit 3, and between the reagent mounting unit 4 and the reaction unit 3. The dispensing system 5 has the dispenser nozzle 50 as shown in FIG. 2. The dispenser nozzle 50 is formed in a rod-shaped tube with stainless or the like, and an end thereof is directed downward and a base thereof is attached to an end of an arm 51. The arm 51 is horizontally arranged, and a base thereof is fixed to an upper end of a support axis 52. The support axis 52 is vertically arranged and is rotated about a vertical axis O as the center by a nozzle moving unit 53. When the support axis 52 is rotated, the arm 51 revolves in a horizontal direction to move the dispenser nozzle 50 in the horizontal direction. Furthermore, the support axis 52 is moved up and down along the vertical axis O by the nozzle moving unit 53. When the support axis 52 moves up and down, the arm 51 is moved up and down in the vertical direction to move the dispenser nozzle 50 up and down in a longitudinal direction of the dispenser nozzle 50, which is the vertical (up-down) direction.

One end of a tube 54a is connected to the base of the dispenser nozzle 50. The other end of this tube 54a is connected to a syringe 55. The syringe 55 has a tubular cylinder 55a, to which the other end of the tube 54a is connected, and a plunger 55b that is provided such that forward and backward sliding movements on an inner wall of the cylinder 55a are possible. The plunger 55b is connected to a plunger driving unit 56. The plunger driving unit 56 is configured with, for example, a liner motor, and enables the forward and backward movements of the plunger 55b relative to the cylinder 55a. One end of a tube 54b is connected to the cylinder 55a of the syringe 55. The other end of this tube 54b is connected to a tank 57 that contains pressurization fluid L1. Furthermore, an electromagnetic valve 58 and a pump 59 are connected on the midway of the tube 54b. As the pressurization fluid L1, noncompressible fluid, such as distilled water or deaerated water, is used. This pressurization fluid L1 is also used as cleaning fluid to clean the inside of the dispenser nozzle 50.

In the dispensing system 5, by driving the pump 59 to bring the electromagnetic valve 58 open, the pressurization fluid L1 contained in the tank 57 is filled in the cylinder 55a of the syringe 55 through the tube 54b. The pressurization fluid L1 is further filled from the cylinder 55a into the end of the dispenser nozzle 50 through the tube 54a. In such a state that the pressurization fluid L1 is filled to the end of the dispenser nozzle 50, the electromagnetic valve 58 is closed and the pump 59 is stopped. When suction of a specimen or a reagent is performed, the plunger driving unit 56 is driven to move the plunger 55b backward relative to the cylinder 55a, thereby applying suction pressure to the end of the dispenser nozzle 50 through the pressurization fluid L1. By this suction pressure, a specimen or a reagent is sucked. When discharge of a specimen or a reagent is performed, the plunger driving unit 56 is driven to move the plunger 55b forward relative to the cylinder 55a, thereby applying discharge pressure to the end of the dispenser nozzle 50 through the pressurization fluid L1. By this discharge pressure, a specimen or a reagent is discharged.

Although not explicitly illustrated in the figure, the dispensing system 5 has a liquid-surface detecting function of detecting a liquid surface of a specimen and a reagent to be dispensed by the dispenser nozzle 50. An example of the fluid-surface detecting function is to detect a liquid surface in accordance with a change in capacitance at the time when the dispenser nozzle 50 touches a specimen or a reagent.

Figure 3:
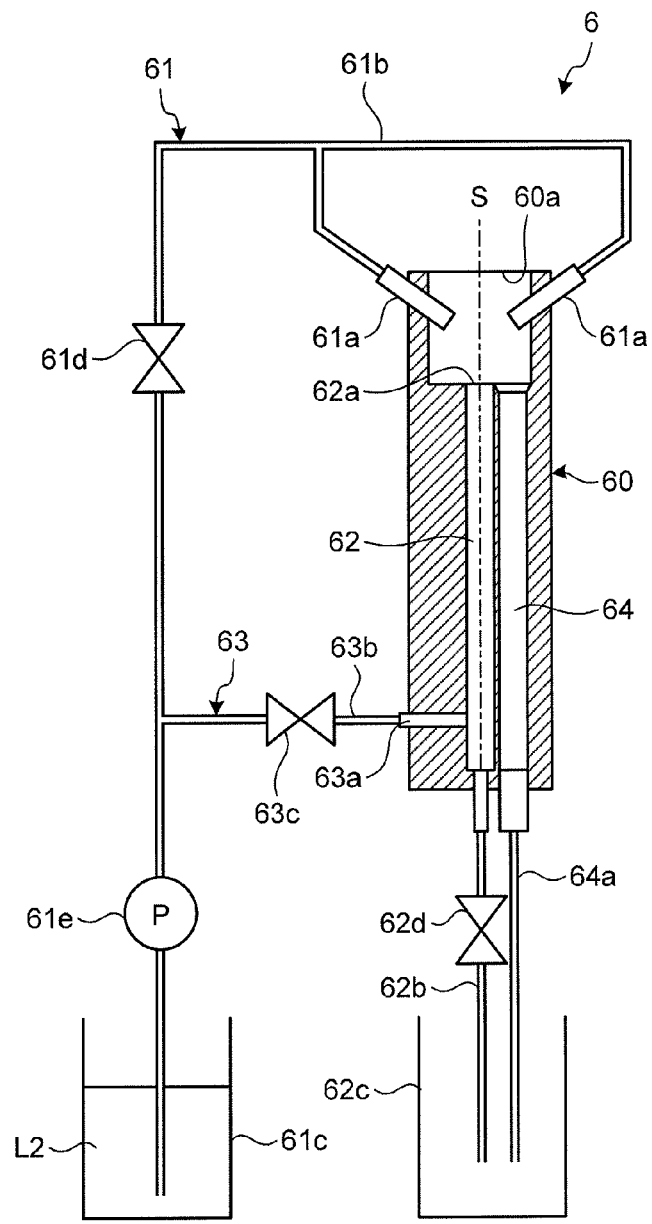
FIG. 3 is a schematic configuration diagram showing a nozzle cleaning device.

The nozzle cleaning device 6 is provided between the reagent mounting unit 4 and the reaction unit 3, at a midway position on a path of the horizontal movement of the dispenser nozzle 50 in the dispensing system 5. The nozzle cleaning device 6 includes a cleaning vessel 60 as shown in FIG. 3. The cleaning vessel 60 is formed in a tubular shape and has an opening 60a at an upper part thereof such that the end of the dispenser nozzle 50 moving downward enters from above.

In the cleaning vessel 60, a jet cleaning-fluid supplier 61 is provided. The jet cleaning-fluid supplier 61 includes nozzles 61a. The plurality of nozzles 61a (two in the present embodiment) are arranged at an upper part in the cleaning vessel 60 directing outlets thereof obliquely downward toward a vertical center line S of the cleaning vessel 60. To each of the nozzles 61a, one end of a branched tube 61b is connected. The tube 61b is formed such that the branches join together on the way from the one ends to the other end. The other end of this tube 61b is connected to a tank 61c that contains cleaning fluid L2. Furthermore, on the midway of the joined tube 61b, an electromagnetic valve 61d and a pump 61e are connected. As the pressurization fluid L2, noncompressible fluid, such as distilled water or deaerated water, is used.

Inside the cleaning vessel 60 and below the nozzle 61a, a retention unit 62 is provided. The retention unit 62 is arranged along the center line S of the cleaning vessel 60 and has an opening 62a at an upper part thereof such that the end of the dispenser nozzle 50 moving downward enters from above. The retention unit 62 is formed to have a bottom so that the cleaning liquid L2 can be retained. To the bottom of the retention unit 62, one end of a tube 62b is connected. The other end of the tube 62b is connected to a waste tank 62c. Also, at a midway of the tube 62b, an electromagnetic valve 62d is connected.

Furthermore, a retention cleaning-fluid supplier 63 is provided in the cleaning vessel 60. The retention cleaning-fluid supplier 63 has a nozzle 63a. The nozzle 63a is arranged near the bottom of the retention unit 62, and an outlet thereof is directed inward of the retention unit 62. To the nozzle 63a, one end of a tube 63b is connected. The other end of the tube 63b is connected to a midway of the tube 61b of the jet cleaning-fluid supplier 61 at a position between the electromagnetic valve 61d and the pump 61e. Furthermore, at a midway of the tube 63b, an electromagnetic valve 63c is connected. That is, the tube 63b is connected to nozzle 63a and then connected to the tube 61b through the electromagnetic valve 63c and is further connected to the tank 61c through the pump 61e.

Furthermore, a drainage unit 64 is provided in the cleaning vessel 60. The drainage unit 64 is arranged inside the cleaning vessel 60 and alongside of the retention unit 62. An opening formed at an upper portion of the drainage unit 64 has a conical shape and a slanting surface thereof is inclined downward from the opening 62a of the retention unit 62. A bottom portion of the drainage unit 64 pierces through the bottom of the cleaning vessel 60. At the bottom portion of the drainage unit 64, one end of a tube 64a is connected. The other end of the tube 64a is connected to the waste tank 62c.

In the nozzle cleaning device 6, by opening the electromagnetic valve 61d and by driving the pump 61e, the cleaning fluid L2 contained in the tank 61c is jet out to the inside of the cleaning vessel 60 from the outlet of the nozzle 61a through the tube 61b. Furthermore, by opening the electromagnetic valve 63c and by driving the pump 61e, the cleaning fluid L2 contained in the tank 61c is supplied into the retention unit 62 from the outlet of the nozzle 63a through the tube 63b and is retained in the retention unit 62. The cleaning fluid L2 that is discharged into the cleaning vessel 60 from the nozzle 61a and the cleaning fluid L2 that is supplied into the retention unit 62 from the nozzle 63a and flows over the opening 62a of the retention unit 62 are guided along the slanting surface of the upper opening of the drainage unit 64 to the inside of the drainage unit 64, and are discharged from the drainage unit 64 through the tube 64a to the waste tank 62c arranged outside of the cleaning vessel 60. Furthermore, by opening the electromagnetic valve 62d, the cleaning fluid L2 retained in the retention unit 62 is discharged to the waste tank 62c through the tube 62b.

In the automatic analyzer 1 thus configured, the dispensing system 5 that is provided between the specimen mounting unit 2 and the reaction unit 3 dispenses a specimen from the specimen vessel 22 to the reaction vessel 32. Moreover, the dispensing system 5 that is provided between the reagent mounting unit 4 and the reaction unit 3 dispenses a reagent from the reagent vessel 42 to the reaction vessel 32. While the reaction vessel 32 to which the specimen and the reagent are dispensed is conveyed by the reaction unit 3 along the circumferential direction, the specimen and the reagent are stirred to react with each other, and then pass between the light source 33a and a photometer sensor 33d. At this time, the reaction liquid in the reaction vessel 32 is measured by the photometer sensor 33d and constituent concentration and the like are analyzed. The reaction vessel 32, for which the analysis is finished, is used again for analysis of a specimen after the cleaning system 34 discharges the reaction liquid, for which the measurement is finished, and cleans the reaction vessel 32.

Figure 4:
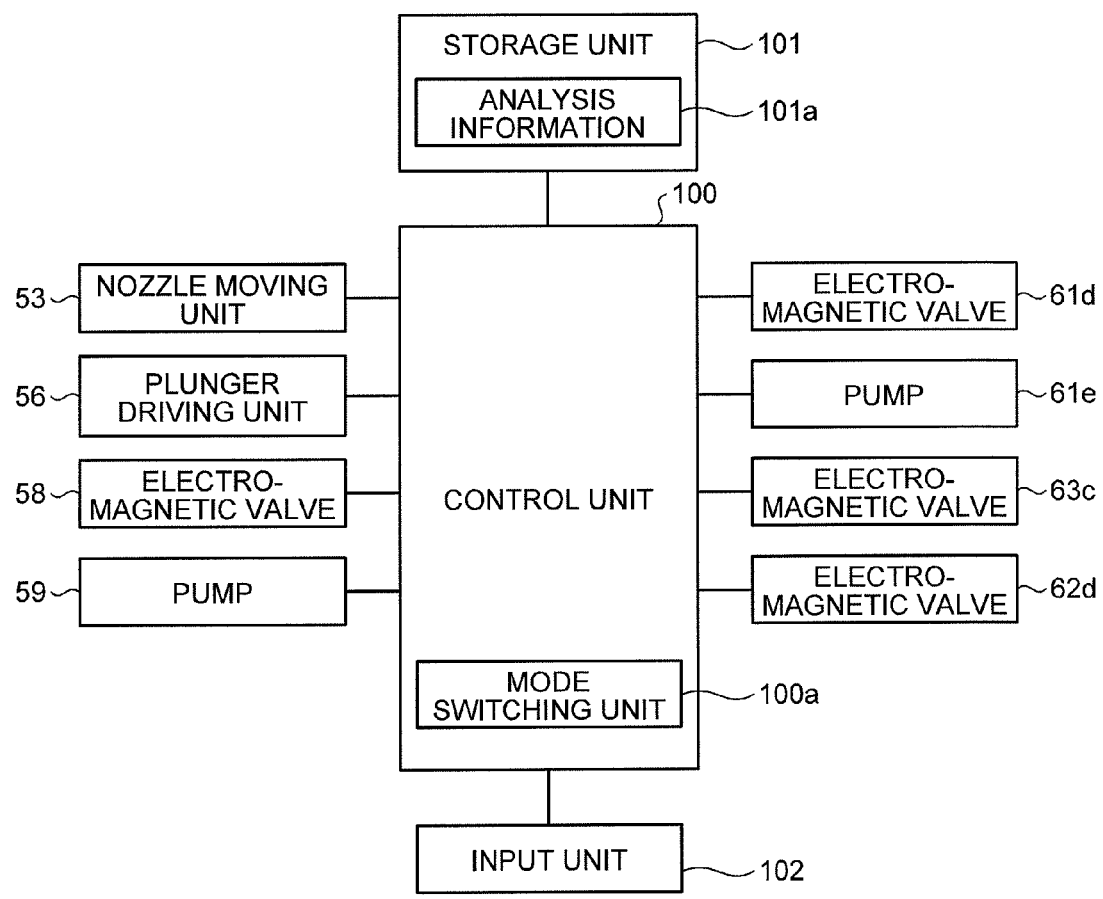
FIG. 4 is a block diagram showing a control system for dispenser nozzle cleaning.

FIG. 4 is a block diagram showing a control system related to dispenser nozzle cleaning. The automatic analyzer 1 has a control unit 100 as shown in FIG. 4. The control unit 100 controls analysis operations of respective components forming the automatic analyzer 1. To the control unit 100, a storage unit 101 and an input unit 102 are connected. Furthermore, the nozzle moving unit 53, the plunger driving unit 56, the electromagnetic valve 58, and the pump 59 of the dispensing system 5 described above are connected to the control unit 100. Further, the electromagnetic valve 61d, the pump 61e, the electromagnetic valve 63c, and the electromagnetic valve 62d of the nozzle cleaning device 6 described above are connected to the control unit 100. The control unit 100 controls the dispensing system 5 and the nozzle cleaning device 6 in accordance with a program and data stored in advance in the storage unit 101 using, particularly, analysis information 101a obtained from the storage unit 101.

To the control unit 100, the analysis information 101a is input by the input unit 102 (for example, the reading unit 23, a keyboard, and a mouse). The analysis information 101a input by the input unit 102 includes a type of a specimen (for example, blood or urine) to be analyzed, an analytical item (for example, analysis of a serum specimen or analysis of a whole blood specimen), immersion depth of the dispenser nozzle 50 from the surface of a specimen at the time of sucking the specimen by the dispenser nozzle 50, and the like. The immersion depth of the dispenser nozzle 50 corresponds to an analytical item, and if the analytical item is analysis of a serum specimen, the depth is to be about several millimeters (for example, 3 mm) from the liquid surface of the specimen, and if the analytical item is analysis of a whole blood specimen, it is to be depth corresponding to the total depth of the specimen (for example, 70% of the entire depth from the liquid surface). The control unit 100 obtains the analysis information 101a, and stores the analysis information 101a in the storage unit 101 associating with the specimen vessel 22 mounted on the specimen mounting unit 2.

The control unit 100 includes a mode switching unit 100a. The mode switching unit 100a switches a cleaning mode for the dispenser nozzle 50. The cleaning mode includes a special cleaning mode and a regular cleaning mode. The special cleaning mode is a mode in which the outer wall of the dispenser nozzle 50 is cleaned after a specimen is sucked and before the specimen is discharged, and the outer wall and the inner wall of the dispenser nozzle 50 are cleaned after the specimen is discharged. The regular cleaning mode is a mode that the outer wall and the inner wall of the dispenser nozzle 50 are cleaned only after the sucked specimen is discharged.

In the control unit 100, in accordance with the above analysis information 101a, the mode switching unit 100a switches the cleaning mode. For example, the mode is switched to the special cleaning mode when the type of a specimen to be analyzed is blood, and the mode is switched to the regular mode when the specimen is urine. Moreover, the mode is switched to the special cleaning mode when the analytical item is analysis of a whole blood specimen, and the mode is switched to the regular cleaning mode when the analytical item is analysis of a serum specimen. Furthermore, the mode is switched to the special cleaning mode when the immersion depth of the dispenser nozzle 50 exceeds a predetermined depth (for example, 3 mm), and the mode is switched to the regular cleaning mode when the immersion depth is equal to or less than the predetermined depth. In switching the cleaning mode by the mode switching unit 100a, the control unit 100 can be configured to switch the cleaning mode using a combination of the analysis information, i.e., the mode is switched to the special cleaning mode when the type of a specimen to be analyzed is blood and the analytical item is analysis of whole blood specimen, for example.

Figure 5:
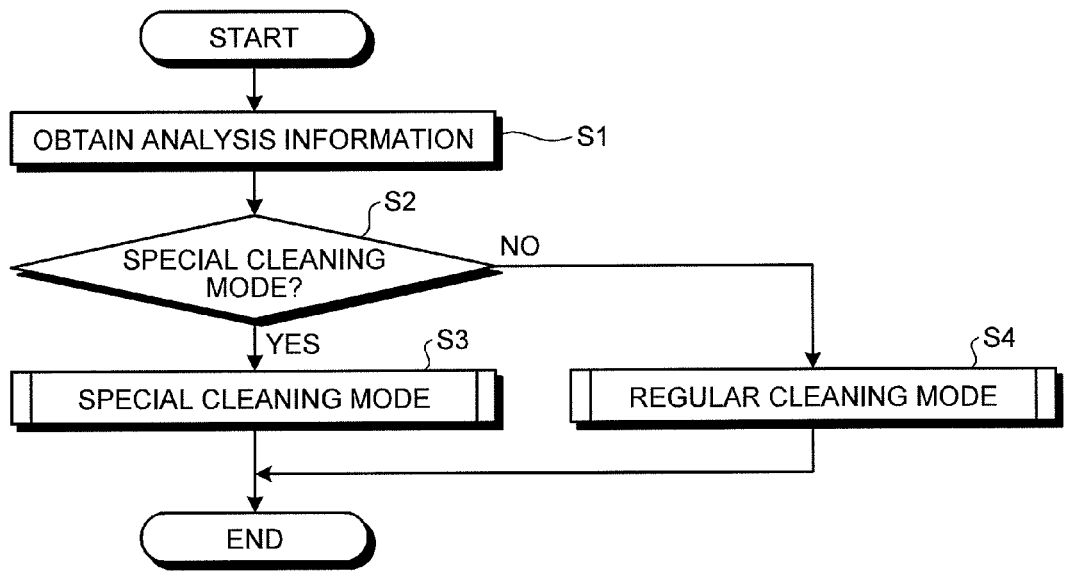
FIG. 5 is a flowchart showing a cleaning operation for a dispenser nozzle.
Figure 7A:
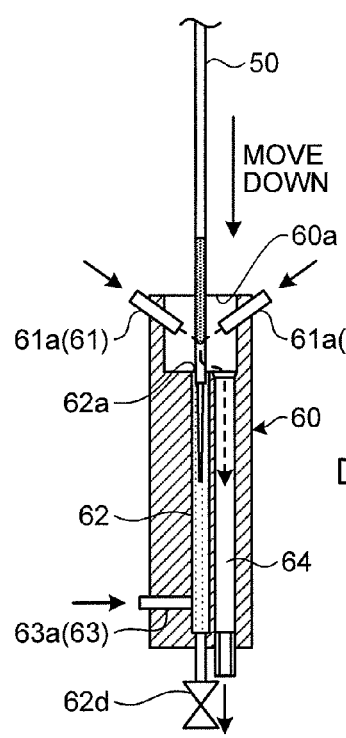
FIGS. 7A to 7C are views showing an operation of the dispenser nozzle in the special cleaning mode.
Figure 7B:
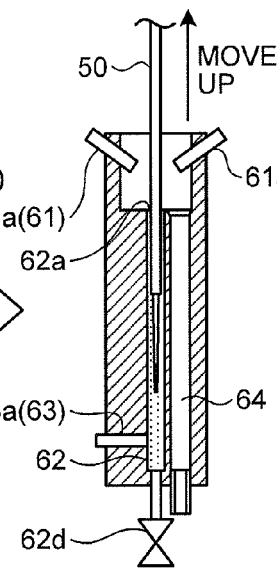
Figure 7C:
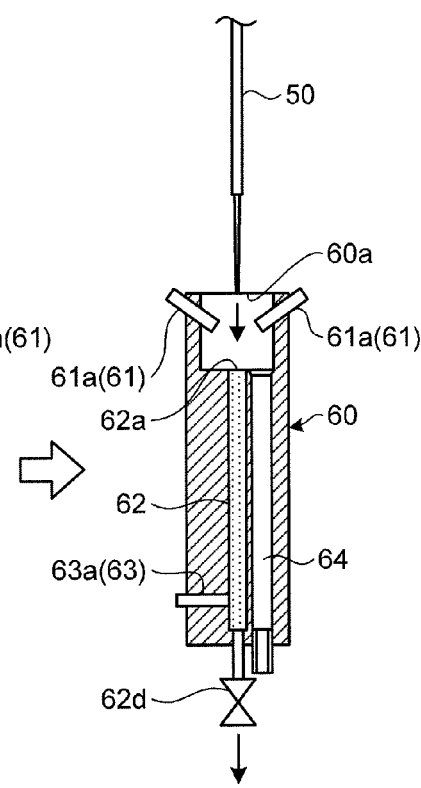
Figure 8:
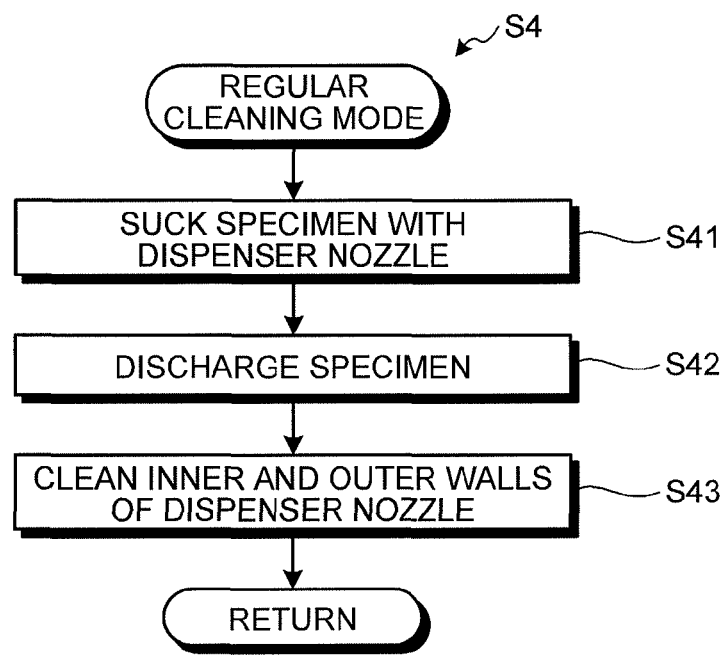
FIG. 8 is a flowchart showing a cleaning operation for the dispenser nozzle by the control unit in a regular cleaning mode.

Dispensation of a specimen by the control unit 100 and cleaning operation for the dispenser nozzle 50 after the dispensation will be described. FIG. 5 is a flowchart showing a cleaning operation for the dispenser nozzle 50 performed by the control unit 100, FIG. 6 is a flowchart showing a cleaning operation for the dispenser nozzle 50 performed by the control unit 100 in the special cleaning mode, FIGS. 7A to 7C show an operation diagram of the dispenser nozzle 50 in the special cleaning mode, and FIG. 8 is a flowchart showing a cleaning operation for the dispenser nozzle 50 performed by the control unit 100 in the regular cleaning mode.

As shown in FIG. 5, the control unit 100 obtains the analysis information 101a from the storage unit 101 (step S1). The control unit 100 switches the cleaning mode by the mode switching unit 100a in accordance with the analysis information 101a (step S2). When the mode is switched to the special cleaning mode at step S2 (step S2: YES), the control unit 100 executes the special cleaning mode as a nozzle cleaning method according to the present embodiment, and finishes the main control (step S3). In contrast, when the mode is switched to the regular cleaning mode at step S2 (step S2: NO), the control unit executes the regular cleaning mode, and finishes the main control (step S4).

Figure 6:
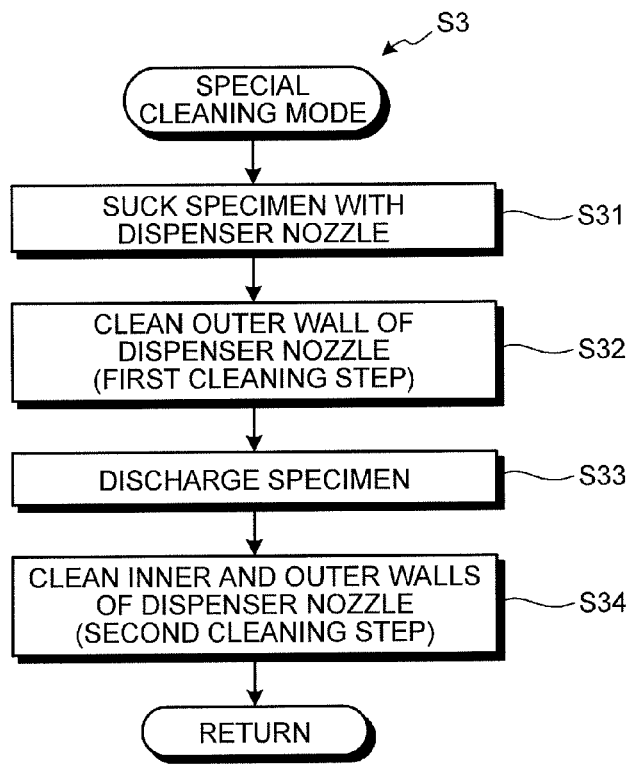
FIG. 6 is a flowchart showing the cleaning operation for the dispenser nozzle by a control unit in a special cleaning mode.

As shown in FIG. 6, in the special cleaning mode (step S3), first, the control unit 100 moves the dispenser nozzle 50 to a position above the opening 22a of the specimen vessel 22 at the specimen sucking position, and controls to suck a specimen with the dispenser nozzle 50 (step S31). Next, the control unit 100 moves the dispenser nozzle 50 to a position above the opening 60a of the cleaning vessel 60 in the nozzle cleaning device 6, and causes the nozzle cleaning device 6 to clean the outer wall of the dispenser nozzle 50 before discharge of the sucked specimen, as a first cleaning step (step S32). Subsequently, the control unit 100 moves the dispenser nozzle 50 to a position above the reaction vessel 32 at a specimen discharging position, and controls to discharge a predetermined amount of the specimen in accordance with the analysis information 101a (step S33). Thus, the dispensation of the specimen to the reaction vessel 32 is finished. Finally, the control unit 100 moves the dispenser nozzle 50 to a position above the opening 60a of the cleaning vessel 60 in the nozzle cleaning device 6, and causes the nozzle cleaning device 6 to clean the inner wall and the outer wall of the dispenser nozzle 50 as a second cleaning step (step S34).

At the first cleaning step (step S32) in the special cleaning mode (step S3) described above, the control unit 100 first causes the jet cleaning-fluid supplier 61 to supply the cleaning fluid L2 from the nozzle 61a to the upper portion in the cleaning vessel 60, and closes the electromagnetic valve 62d of the retention unit 62 and causes the retention cleaning-fluid supplier 63 to supply the cleaning fluid L2 from the nozzle 63a to the retention unit 62. In this state, the control unit 100 brings the dispenser nozzle 50 down to insert into the opening 60a of the cleaning vessel 60. Accordingly, the dispenser nozzle 50 moves downward along the longitudinal direction thereof while entering a flow path of the cleaning fluid L2 supplied from the nozzle 61a. Thus, the cleaning fluid jet out from the nozzle 61a collides with the outer wall of the dispenser nozzle 50 along the longitudinal direction of the dispenser nozzle 50, to remove the specimen adhered on the outer wall of the dispenser nozzle 50, and as a result, the outer wall of the dispenser nozzle 50 is cleaned. The removed specimen is drained to the outside of the cleaning vessel 60 by the drainage unit 64.

Further, the dispenser nozzle 50 is inserted into the retention unit 62. Accordingly, the dispenser nozzle 50 is immersed into the cleaning fluid L2 retained in the retention unit 62, and the outer wall of the dispenser nozzle 50 is further cleaned. In the retention unit 62, the cleaning fluid L2 that flow out from the opening 62a while being supplied from the nozzle 63a is drained to the outside of the cleaning vessel 60 by the drainage unit 64. Therefore, the contaminated cleaning fluid L2 containing the removed specimen is drained without staying in the retention unit 62, and the clean cleaning fluid L2 is always supplied to the retention unit 62. Thus, the contaminated cleaning fluid L2 is not to adhere to the dispenser nozzle 50. The depth to which the dispenser nozzle 50 is inserted into the retention unit 62 can be any depth equal to or deeper than the depth to which the dispenser nozzle 50 has been immersed into the specimen at the time of sucking the specimen.

Next, the control unit 100 moves the dispenser nozzle 50 upward to take out the dispenser nozzle 50 from the retention unit 62 as shown in FIG. 7B. At this time, supply of the cleaning fluid L2 by the jet cleaning-fluid supplier 61 and the retention cleaning-fluid supplier 63 can be stopped. The supply of the cleaning fluid L2 by the jet cleaning-fluid supplier 61 can be continued so as to further clean the outer surface of the dispenser nozzle 50 moving upward along the longitudinal direction of the dispenser nozzle 50 in a state where the dispenser nozzle 50 is in the flow path of the cleaning fluid L2 supplied from the nozzle 61a.

Subsequently, the control unit 100 discharges a portion of the specimen present in the dispenser nozzle 50 to discard the portion. This enables to discard the cleaning fluid L2 adhered at the end of the dispenser nozzle 50 by the above-described cleaning, together with the discharged specimen. Therefore, it is possible to prevent the cleaning fluid L2 from being mixed with a specimen to be discharged into the reaction vessel 32. Finally, the control unit 100 draws the dispenser nozzle 50 out from the cleaning vessel 60 and drains the cleaning fluid L2 that has been retained in the retention unit 62 by opening the electromagnetic valve 62d of the retention unit 62, to finish the cleaning at step S32.

Moreover, although not explicitly illustrated in the figure, at the second cleaning step (step S34) in the special cleaning mode (step S3) described above, the control unit 100 discharges the cleaning fluid (pressurization fluid L1) filled in the dispenser nozzle 50 together with the specimen to discard into the cleaning vessel 60, and cleans the inner wall of the dispenser nozzle 50. Next, the control unit 100 supplies the cleaning fluid L2 from the nozzle 61a of the jet cleaning-fluid supplier 61, and moves the dispenser nozzle 50 down to insert into the opening 60a of the cleaning vessel 60, thereby cleaning the outer wall of the dispenser nozzle 50 with the cleaning fluid L2 supplied from the nozzle 61a. Furthermore, the dispenser nozzle 50 moving down is inserted into the retention unit 62 to be immersed in the cleaning fluid L2 retained in the retention unit 62, and the outer wall of the dispenser nozzle 50 is further cleaned. Finally, the control unit 100 draws the dispenser nozzle 50 out from the cleaning vessel 60, to finish the cleaning at step S34.

At above step S34, for the dispenser nozzle 50, cleaning of the outer wall can be performed only with the cleaning fluid L2 supplied from the jet cleaning-fluid supplier 61. In this case, the cleaning fluid L2 is not supplied from the retention cleaning-fluid supplier 63, and the electromagnetic valve 62d of the retention unit 62 is opened to drain the cleaning fluid L2 that has flowed into the retention unit 62. Alternatively, at step S34, the outer surface of the dispenser nozzle 50 can be cleaned just by inserting the dispenser nozzle 50 into the retention unit 62 without supplying the cleaning fluid L2 from the jet cleaning-fluid supplier 61. Furthermore, at step S34, only the cleaning of the inner wall of the dispenser nozzle 50 can be performed because the outer wall of the dispenser nozzle 50 has already been cleaned at step S32, and the inner wall of the dispenser nozzle 50 can be cleaned only by discharging the cleaning fluid (pressurization fluid L1) filled in the dispenser nozzle 50 together with the specimen to be discarded into the cleaning vessel 60, without supplying the cleaning fluid L2 from the jet cleaning-fluid supplier 61 and the retention cleaning-fluid supplier 63.

As shown in FIG. 8, in the regular cleaning mode (step S4), first, the control unit 100 moves the dispenser nozzle 50 to a position above the opening 22a of the specimen vessel 22 at the specimen sucking position, and controls to suck the specimen with the dispenser nozzle 50 (step S41). Next, the control unit 100 moves the dispenser nozzle 50 to a position above the reaction vessel 32 at the specimen discharging position, to discharge the specimen (step S42). Thus, the dispensation of the specimen into the reaction vessel 32 is finished. Finally, the control unit 100 moves the dispenser nozzle 50 to a position above the opening 60a of the cleaning vessel 60 in the nozzle cleaning device 6, and causes the nozzle cleaning device 6 to clean the inner wall and the outer wall of the dispenser nozzle 50 similarly to the second cleaning step (step S34) in the special cleaning mode described above (step S43).

When a specimen is dispensed with the dispenser nozzle 50, and the dispenser nozzle 50 is cleaned and dispensation of a next specimen is performed, it is demanded that cleaning is achieved until carry over to the next specimen is equal to or less than 0.1 ppm, at which there is no risk of carrying a pathogenic causing an infectious disease. In the above special cleaning mode of the present embodiment, a result obtained when carry over was measured in a case where the end of the dispenser nozzle 50 was immersed to the deepest point in the specimen vessel 22 when the dispensation amount of a whole blood specimen is 10 mL was that carry over to the next specimen was within a range from 0.002 ppm to 0.018 ppm, and the demand that carry over be 0.1 ppm or less was satisfied.

As described, according to the nozzle cleaning method by the automatic analyzer 1 described above, the first cleaning step in which the outer wall of the dispenser nozzle 50 is cleaned after a specimen is sucked and before the specimen is discharged, and the second cleaning step in which at least the inner wall of the dispenser nozzle 50 is cleaned after the specimen is discharged are included. Therefore, when dispensation of a specimen such as a whole blood specimen, which includes a coagulation component and has viscosity, is performed, the dispenser nozzle 50 is cleaned immediately after the dispenser nozzle 50 is in contact with the specimen and before the specimen coagulates to adhere on the outer wall of the dispenser nozzle 50 as a result of exposure to air in the first cleaning step. Thus, the dispenser nozzle 50 can be easily cleaned so well that carry over can be avoided. In the second cleaning step performed thereafter, the outer wall of the dispenser nozzle 50 has been cleaned in the first cleaning step, and the inner wall of the dispenser nozzle 50 in which the specimen has been held in a state where the specimen is less prone to be exposed to air is cleaned, and therefore, cleaning of the dispenser nozzle 50 can be performed easily. As a result, by reliably cleaning the dispenser nozzle 50 to avoid carry over, thereby preventing prolongation of the entire cleaning time for the dispenser nozzle 50. Therefore, it is possible to avoid lengthening time required for a dispensation cycle, which includes suction and discharge of a specimen and cleaning of the dispenser nozzle 50, and an analysis speed can be increased.

Moreover, after the dispenser nozzle 50 is cleaned in the first cleaning step, a portion of the specimen held in the dispenser nozzle 50 is discarded. Therefore, although it is considered that the cleaning fluid L2 is brought into contact with a specimen that has been sucked to be in the dispenser nozzle 50 to be mixed with the specimen at the time of cleaning the outer wall of the dispenser nozzle 50 after the specimen is sucked and before the specimen is discharged, the cleaning fluid L2 is discarded together with the discarded portion of the specimen. Therefore, mixture of the cleaning fluid L2 into the specimen to be discharged into the reaction vessel 32 is avoided, and analysis is not affected thereby. Furthermore, because the cleaning fluid L2 adhered on the outer wall at the end of the dispenser nozzle 50 is also discarded accompanying discard of a portion of the specimen, mixture of the cleaning fluid L2 that adheres on the outer wall at the end of the dispenser nozzle 50 into the specimen to be discharged into the reaction vessel 32 can also be avoided.

Moreover, in the first cleaning step described above, the dispenser nozzle 50 is moved downward or upward in the longitudinal direction while having the dispenser nozzle 50 entered into the flow path of the cleaning fluid L2 jet out from the nozzle 61a of the jet cleaning-fluid supplier 61. Accordingly, the cleaning fluid jet out from the nozzle 61a collides with the outer wall of the dispenser nozzle 50 along with the longitudinal direction of the dispenser nozzle 50, and the outer wall of the dispenser nozzle 50 is cleaned. Therefore, even if the specimen adheres in a relatively wide range in the longitudinal direction from the end to the base of the dispenser nozzle 50, cleaning of this dispenser nozzle 50 can be reliably performed.

Furthermore, in the first cleaning step, the dispenser nozzle 50 is entered along with the movement of the dispenser nozzle 50 in the longitudinal direction into the retention unit 62 in which the cleaning fluid L2 supplied by the retention cleaning-fluid supplier 63 is retained. Therefore, in addition to the cleaning with the cleaning fluid L2 that is supplied from the nozzle 61a, the outer wall of the dispenser nozzle 50 is immersed in the cleaning fluid in the retention unit 62 to be further cleaned. Therefore, even if the specimen adheres in a relatively wide range from the end to the base of the dispenser nozzle 50, cleaning of this dispenser nozzle 50 can be reliably performed.

The nozzle cleaning device 6 of the automatic analyzer 1 includes the cleaning vessel 60 that has the opening 60a, to which the dispenser nozzle 50 is inserted, at an upper part; the jet cleaning-fluid supplier 61 that has the nozzle 61a from which the cleaning fluid L2 is jet out at an upper part in the cleaning vessel 60; the retention unit 62 that is arranged in the cleaning vessel 60 at a position below the nozzle 61a of the jet cleaning-fluid supplier 61 and retains the cleaning fluid L2, the retention unit 62 having the opening 62a, to which the dispenser nozzle 50 is inserted, at an upper part; and the retention cleaning-fluid supplier 63 that supplies the cleaning fluid L2 into the retention unit 62. In the nozzle cleaning device 6, when the dispenser nozzle 50 is cleaned, the dispenser nozzle 50 is inserted into the opening 60a at the upper part of the cleaning vessel 60, and accordingly, the outer wall of the dispenser nozzle 50 is cleaned with the cleaning fluid L2 that is jet out from the nozzle 61a at an upper part in the cleaning vessel 60. After this cleaning, the dispenser nozzle 50 is inserted into the retention unit 62, and the outer wall of the dispenser nozzle 50 is further cleaned with the cleaning fluid L2 supplied to the retention unit 62 from the retention cleaning-fluid supplier 63. Therefore, even if the specimen adheres in a relatively wide range from the end to the base of the dispenser nozzle 50, cleaning of this dispenser nozzle 50 can be reliably performed. In addition, by moving the dispenser nozzle 50 downward once, two cleanings are performed, and therefore, extension of the cleaning time can be prevented. As a result, it is possible to avoid lengthening time required for a dispensation cycle, which includes suction and discharge of a specimen and cleaning of the dispenser nozzle 50, and an analysis speed can be increased.

Moreover, the nozzle cleaning device 6 has the drainage unit 64 that drains the cleaning fluid L2 that is supplied by the jet cleaning-fluid supplier 61 and the cleaning fluid L2 that is supplied by the retention cleaning-fluid supplier 63 and that flows out from the opening 62a of the retention unit 62, to the outside of the cleaning vessel 60. Therefore, the cleaning fluid L2 that is supplied from the nozzle 61a of the jet cleaning-fluid supplier 61 and that contains the specimen removed from the outer wall of the dispenser nozzle 50 is drained by the drainage unit 64, and the cleaning fluid L2 that flows out from the retention unit 62 and that contains the specimen removed from the outer wall of the dispenser nozzle 50 is drained by the drainage unit 64. As a result, the cleaning fluid L2 not containing the removed specimen is retained in the retention unit 62, and therefore, re-adhesion of the removed specimen to the dispenser nozzle 50 is prevented.

According to the automatic analyzer 1 described above, the mode switching unit 100a is provided that has the special cleaning mode in which the outer wall of the dispenser nozzle 50 is cleaned after a specimen is sucked and before the specimen is discharged, and at least the inner wall of the dispenser nozzle 50 is cleaned after the sucked specimen is discharged, and the regular cleaning mode in which the outer wall and the inner wall of the dispenser nozzle 50 are cleaned only after the sucked specimen is discharged. The mode switching unit 100a switches between the special cleaning mode and the regular cleaning mode in accordance with the analysis information 101a obtained in advance. In this automatic analyzer 1, in accordance with the analysis information 101a, the mode is switched to the special cleaning mode, for example, when the cleaning time is required to be long for cleaning after dispensation of a specimen, such as a whole blood specimen that contains a coagulation component and that has viscosity. The mode is switched to the regular cleaning mode, for example, when the cleaning time can be maintained short even for cleaning after dispensation of a specimen, such as a serum specimen for which cleaning of the outer wall of the dispenser nozzle 50 is relatively easy. Thus, the cleaning mode can be switched so that extension of the entire cleaning time is avoided, corresponding to condition of analysis of a specimen. As a result, it is possible to avoid lengthening time required for a dispensation cycle, which includes suction and discharge of a specimen and cleaning of the dispenser nozzle 50, and an analysis speed can be increased.

Furthermore, the analysis information includes a type of a specimen to be analyzed, an analytical item, and immersion depth of the dispenser nozzle from the fluid surface at the time of sucking a specimen, and the mode switching unit switches the cleaning mode in accordance with at least one of the analysis information, or on a combination thereof, thereby achieving selection of the cleaning mode that matches the condition of analysis of a specimen.

Although the automatic analyzer 1 has been explained in the case where the dispenser nozzle is cleaned when a specimen is dispensed using the nozzle cleaning method and the nozzle cleaning device 6, it is applicable also when the dispenser nozzle that has dispensed a reagent is cleaned.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A nozzle cleaning method comprising:
a first cleaning step including cleaning an outer wall of a dispenser nozzle after liquid is sucked into the nozzle and before the liquid is discharged from the nozzle; and
a second cleaning step including cleaning at least an inner wall of the dispenser nozzle after the liquid is discharged,
wherein the first cleaning step includes inserting the dispenser nozzle into a retention unit in which cleaning fluid is retained, and flowing out cleaning fluid from an opening of the retention unit which retains the cleaning fluid to outside of a cleaning vessel in which the nozzle cleaning is conducted.

2. The nozzle cleaning method according to claim 1, wherein the first cleaning step includes, after the dispenser nozzle is cleaned, discarding a portion of the liquid sucked into the dispenser nozzle.

3. The nozzle cleaning method according to claim 1, wherein the first cleaning step includes moving the dispenser nozzle in a longitudinal direction thereof while having the dispenser nozzle entered into a flow path of cleaning fluid being jet out.

4. The nozzle cleaning method according to claim 2, wherein the first cleaning step includes moving the dispenser nozzle in a longitudinal direction thereof while having the dispenser nozzle entered into a flow path of cleaning fluid being jet out.

* * * * *